United States Patent
Sorensen et al.

(10) Patent No.: US 7,020,578 B2
(45) Date of Patent: Mar. 28, 2006

(54) METHOD FOR EVALUATING NOVEL, STROKE TREATMENTS USING A TISSUE RISK MAP

(75) Inventors: Gregory A. Sorensen, Lexington, MA (US); Ona Wu, Utrecht (NL)

(73) Assignee: The General Hospital Corporation, Boston, MA (US)

( * ) Notice: Subject to any disclaimer, the term of this patent is extended or adjusted under 35 U.S.C. 154(b) by 219 days.

(21) Appl. No.: 10/182,978

(22) PCT Filed: Feb. 2, 2001

(86) PCT No.: PCT/US01/03502

§ 371 (c)(1),
(2), (4) Date: Mar. 4, 2003

(87) PCT Pub. No.: WO01/56466

PCT Pub. Date: Aug. 9, 2001

(65) Prior Publication Data

US 2004/0127799 A1 Jul. 1, 2004

Related U.S. Application Data

(60) Provisional application No. 60/179,654, filed on Feb. 2, 2000.

(51) Int. Cl.
*A61B 5/055* (2006.01)

(52) U.S. Cl. .................. 702/181; 424/9.36; 600/410
(58) Field of Classification Search ............... 702/181; 600/410, 411, 419, 420, 407; 424/9.1, 9.2, 424/9.3, 9.34, 9.36
See application file for complete search history.

(56) References Cited

U.S. PATENT DOCUMENTS

| | | | | |
|---|---|---|---|---|
| 5,230,346 A | | 7/1993 | Leuchter et al. | |
| 5,494,655 A | * | 2/1996 | Rocklage et al. | 424/9.36 |
| 5,796,759 A | | 8/1998 | Eisenberg et al. | |
| 5,914,112 A | * | 6/1999 | Bednar et al. | 424/144.1 |
| 5,993,388 A | | 11/1999 | Kattan et al. | |
| 6,346,229 B1 | * | 2/2002 | Driehuys et al. | 424/9.36 |
| 6,463,315 B1 | * | 10/2002 | Klingberg et al. | 600/410 |
| 6,491,895 B1 | * | 12/2002 | Driehuys et al. | 424/9.36 |
| 6,546,275 B1 | * | 4/2003 | Carroll | 600/419 |
| 6,567,684 B1 | * | 5/2003 | Chenevert et al. | 600/410 |
| 6,618,607 B1 | * | 9/2003 | Song | 600/410 |
| 6,700,374 B1 | * | 3/2004 | Wu et al. | 324/312 |
| 2001/0000727 A1 | * | 5/2001 | Driehuys et al. | 424/9.36 |
| 2001/0037063 A1 | * | 11/2001 | Albert et al. | 600/420 |
| 2002/0001574 A1 | * | 1/2002 | Woiff et al. | 424/93.1 |
| 2002/0081294 A1 | * | 6/2002 | Bednar et al. | 424/143.1 |
| 2002/0103429 A1 | * | 8/2002 | deCharms | 600/410 |
| 2003/0064023 A1 | * | 4/2003 | Driehuys et al. | 424/9.3 |
| 2003/0152516 A1 | * | 8/2003 | Driehuys et al. | 424/9.3 |

OTHER PUBLICATIONS

K.M.A. Welch, MD, et al. "A Model to Predict the Histopathology of Human Stroke Using Diffusion and $T_2$-Weighted Magnetic Resonance Imaging", Diffusion Imaging in Stroke, vol. 26, No. 11, Nov. 1995, pp. 1983–1989.

* cited by examiner

*Primary Examiner*—Carol S. W. Tsai
(74) *Attorney, Agent, or Firm*—Daly, Crowley, Mofford & Durkee, LLP.

(57) ABSTRACT

A method of evaluating novel stroke treatments includes generating a risk map indicative of the probability of tissue infarction on voxel-by-voxel basis and selecting a probability range for evaluating the therapeutic effect of the novel treatment. In one particular embodiment, tissue having a fifty percent probability of tissue infarction is selected. A novel treatment that has a reduced level of overall actual infarction as compared to the predicted value is indicative of therapeutic effect.

18 Claims, 10 Drawing Sheets

METHOD FOR EVALUATING NOVEL, STROKE TREATMENTS USING A TISSUE RISK MAP

CROSS-REFERENCE TO RELATED APPLICATIONS

This application claims priority from PCT Application No. US01/03502 filed on Feb. 2, 2001, which claims the benefit of U.S. Provisional Application No. 60/179,654 filed on Feb. 2, 2000, both of which are incorporated herein by reference.

STATEMENT REGARDING FEDERALLY SPONSORED RESEARCH

The invention was sponsored by NIH Grant No. PO1 NS35611-03. The government may have certain rights in the invention.

FIELD OF THE INVENTION

The present invention relates generally to medical imaging and, more particularly, to magnetic resonance imaging.

BACKGROUND OF THE INVENTION

Diffusion-weighted (DWI) and perfusion-weighted (PWI) magnetic resonance (MR) imaging have been shown to be highly sensitive and specific in diagnosing acute human cerebral ischemia. These imaging techniques appear to provide superior early identification of regions likely to proceed to infarction, compared to conventional MR or CT imaging. However, the prediction of tissue and clinical outcome from specific imaging characteristics remains challenging. Although studies have found correlations between acute DWI and PWI with patients' clinical and follow-up imaging outcomes, the ability to predict clinical or tissue outcome in individual patients using a single modality is limited using conventional techniques.

Attempts have been made to combine DWI and PWI by comparing lesion volumes identified by the two techniques. "Diffusion-perfusion mismatches," in which the lesion volumes identified by one modality are larger than those by the other, have been reported by several groups. Some groups have reported larger lesion enlargement of the acute DWI lesion volume in cases where the acute PWI volume is larger than the DWI lesion. In cases where the acute DWI lesion was larger than the PWI lesion, total lesion growth was reduced.

However, these reported "mismatches" are of volumes of tissue rather than a voxel-by-voxel comparison. Heterogeneity in both apparent diffusion coefficient (ADC) and flow values within acute ischemic tissue in humans have been well documented but have not been captured in these initial volumetric approaches. Therefore, volumetric approaches comparing gross differences in DWI and PWI lesion volumes may oversimplify the complex task of assessing tissue viability in different regions within ischemic tissue.

One known voxel-by-voxel was developed by Welch et al., "A Model to Predict the Histopathology of Human Stroke Using Diffusion and T2-Weighted Magnetic Resonance Imaging," Stroke. 1995;26:1983–1989. Welch's approach provide a more sensitive approach for identifying salvageable tissue by demonstrating that a combination of T2 and ADC information provided better prediction of cellular necrosis than algorithms that used them separately and that a voxel-by-voxel analysis may better demonstrate the underlying heterogeneity in the lesion. These studies implemented their predictive algorithms using thresholding techniques in which tissue is classified as abnormal if a measured value, e.g., the apparent diffusion coefficient (ADC) or T2WI value, is 1.5–2 standard deviations away from its mean value in the contralateral hemisphere. Readily assessing the signatures' significance can therefore be complicated as the number of input parameters is increased (d inputs result in 2d states). Another potential problem with a thresholding algorithm is that it ignores the variances intrinsic in the input data. A more appropriate model may be one in which the inputs are considered random variables and the output a probability variable.

It would, therefore, be desirable to provide a voxel-by-voxel risk map indicating the probabilities that tissue will infarct. It would further be desirable to utilize the risk map to evaluate novel interventions.

SUMMARY OF THE INVENTION

The present invention provides a method for utilizing a risk map indicating the probability of tissue infarction to evaluate the efficacy of novel interventions for human cerebral ischemia. In one embodiment, diffusion weighted image (DWI) data and perfusion weighted image (PWI) data is obtained from an acute stroke patient within a predetermined time of symptom onset. A risk map is then generated from the acquired data. In one particular embodiment, a generalized linear model (GLM) algorithm combines diffusion weighted image (DWI) data and perfusion weighted image (PWI) data to generate a risk map of tissue infarction. Coefficients for the GLM algorithm are optimized by training the algorithm with DWI and PWI image data, which can include follow-up imaging studies to confirm the extent of the final infarct volume.

After application of the novel treatment, the level of actual tissue infarction is compared to the level of predicted tissue infarction at predetermined times. Where the actual level of tissue infarction is less than predicted by the risk map, this can provide some evidence of a statistically significant therapeutic effect from the novel intervention.

In another aspect of the invention, DWI and PWI data is acquired from a patient acutely. The data is used to generate a first risk map corresponding to a first treatment, which can be a conventional treatment, and a second risk map corresponding to a second treatment. Further risk maps can be generated for further treatment options. Based upon the output from the risk maps, a treatment having the highest predicted efficacy can be selected. Efficacy can be based upon a variety of factors including volume reduction of tissue at risk and reduction of risk values.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention combines data from a plurality of acute imaging techniques using statistical methodology to generate a risk map of tissue infarction for evaluating novel treatments. In one particular application, perfusion and diffusion MRI image data are combined to evaluate potential stroke treatments. More particularly, statistical algorithms are used to evaluate the risk of infarction for each voxel of tissue.

In general, a tissue infarction risk map is generated from image data acquired from a patient within a predetermined amount of time of symptom onset. Image data can include conventional MR imaging data, e.g. T2-weighted FSE, diffusion weighted image (DWI) data, such as apparent diffusion coefficient (ADC) data, anisotropy indices, and other combinations of eigenvalues and eigenvectors, and perfusion weighted image (PWI) data such as cerebral blood volume (CBF), cerebral blood volume (CBV), and mean transit time (MTT) to name a few of the parameters derived from the contrast-enhanced images.

The risk map can be generated from acquired acute imaging data using a variety of techniques including linear generalized models (GLMs), general additive models (GAMs) and neural networks. In one embodiment, a generalized linear model (GLM) is used to combine DWI and PWI data. The GLM can be used to define a probability of tissue infarction y as set forth in Equation 1 below:

$$y = \frac{1}{1 + e^{-\beta x}}, \quad \text{Eq. (1)}$$

where y ranges between 0 and 1.0, x is set of image data, e.g., x={T2, ADC, CBF, CBV, MTT}, and β represents coefficients calculated using a curve fitting algorithm, such as iterative reweighted least squares.

Figure 1:
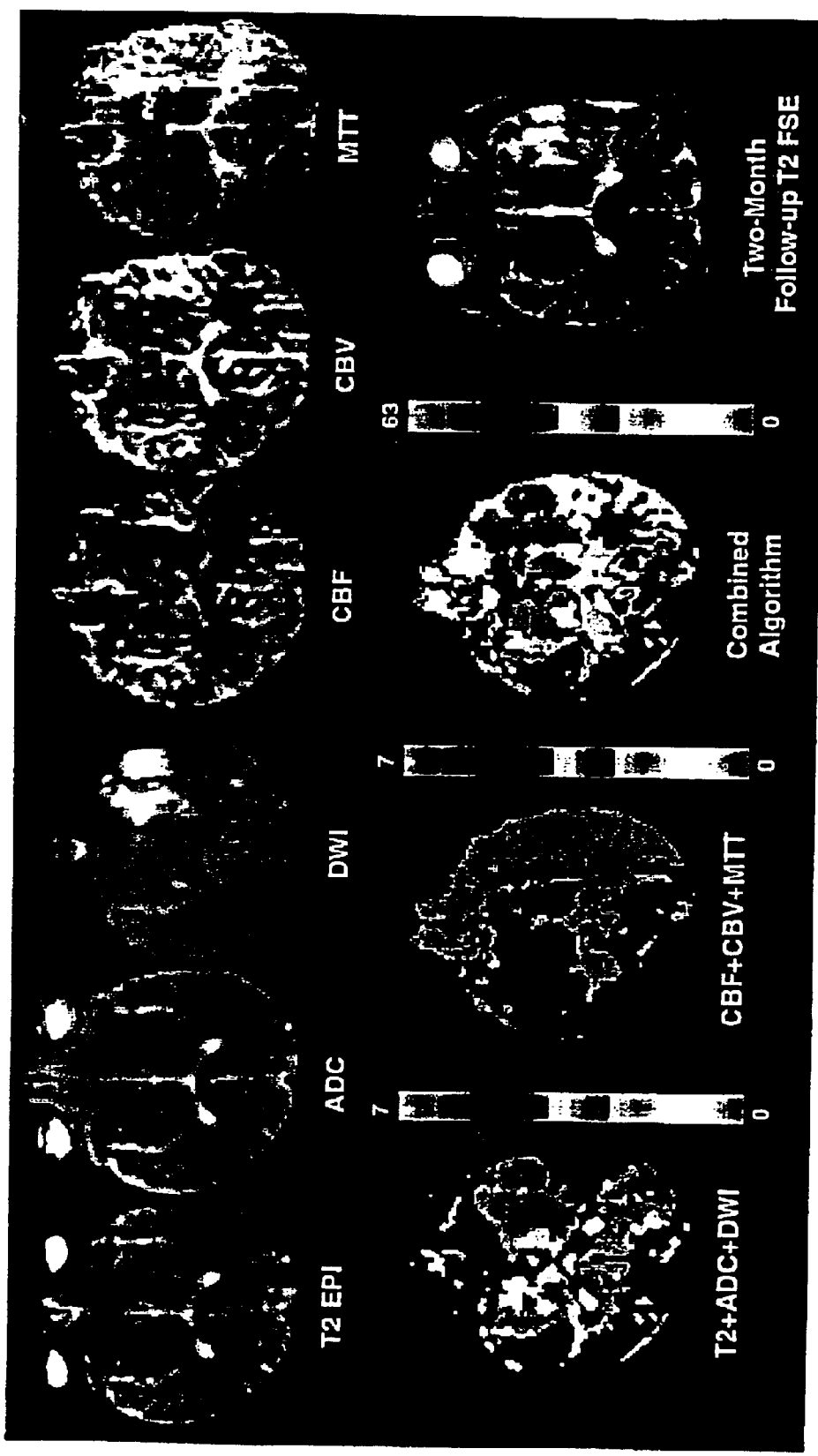
FIG. 1 shows acute DWI and PWI data images including a risk map for a patient receiving conventional treatment that can be used for evaluating novel treatments in accordance with the present invention.

FIG. 1 shows a series of images including low b, ADC, CBF, CBV, MTT, DWI, PWI and an exemplary risk map 100 (combined DWI+PWI) indicating a probability of tissue infarction on a voxel-by-voxel basis. That is, for each voxel the map indicates a probability that the corresponding tissue will go on to infarction. As shown, certain regions if tissue have a relatively high probability of infarction. A follow up T2 image shows regions of actual infarction. As described in detail below, the risk map 100 can be used to evaluate the efficacy of novel stroke treatments by comparing predicted infarction and actual infarction.

EXAMPLE 1

Diffusion-weighted (DWI) and perfusion-weighted MR images (PWI) from acute stroke patients scanned within twelve hours of symptom onset were retrospectively studied and used to develop thresholding and generalized linear model (GLM) algorithms predicting tissue outcome as determined by follow-up MRI. The performances of the algorithms were evaluated for each patient by using receiver operating characteristic (ROC) curves.

Imaging was performed on a 1.5T General Electric Signa MR instrument, with version 5.4.2 software made by General Electric Medical Systems, Waukesha, Wis. and retrofitted with echo planar imaging (EPI) capabilities via an Advanced NMR Systems of Wilmington, Mass., hardware upgrade that included the "catch and hold" modification. MR acquisition parameters for the patients include all diffusion sequences acquired axially at TR=6000, b-value= 1221 s/mm$^2$ up to 20 slices and perfusion sequences with TR/TE=1500/75 ms, 11 slices and 46 timepoints.

Multi-slice axial diffusion-weighted images were acquired by either sampling three orthogonal directions at b-values of 1010 s/mm$^2$ (n=3) or sampling the full diffusion tensor at b-values of 1221 s/mm$^2$ (n=11) using single-shot pulsed field gradient spin echo EPI using imaging parameters. The isotropic diffusion weighted image (DWI) was formed from the geometric mean of the high b-value single-shot images. The ADC image was calculated from the slope of the linear regression fit of the log of the high and low b-value images versus their b-values.

Perfusion weighted images were acquired from dynamic susceptibility contrast images using either spin-echo (SE) (n=10) or gradient-echo (GRE) (n=4) EPI pulse sequences. Images were acquired during the first pass of a bolus of 0.1 mmol/kg (GRE) or 0.2 mmol/kg (SE) of body weight of gadopentetate dimeglumine contrast agent (Magnevist; Berlex Laboratories, Wayne, N.J.) injected with a MRI-compatible power injector (Medrad, Pittsburgh, Pa.). For both the diffusion and perfusion studies, the FOV was 400×200 mm$^2$ with an acquisition matrix of 256×128 acquired with a slice thickness of 6 mm and a 1 mm interslice gap. Relative regional cerebral blood volume (CBV), relative cerebral blood flow (CBF) and mean transit time (MTT) maps were calculated using well known techniques. Each patient was also imaged with conventional sequences following a standard acute stroke protocol, such as that used at Massachusetts General Hospital.

The volumetric diffusion, perfusion and follow-up data were spatially coregistered utilizing an automated image registration software package, AIR 3.08 (UCLA, CA). The initial low b-value T2-weighted EPI, ADC, DWI and follow-up T2-weighted FSE images were coregistered to the same dimensions (128×128×11 or 128×128×10 voxels), orientation, and coordinates as the perfusion images using an affine, twelve-parameter transformation model and trilinear interpolation. Voxels from "normal" appearing gray matter in the unaffected, contralateral hemisphere from the coregistered initial T$_2$ images were outlined prior to generation of the predictive maps. For all six acute-stage images, voxel values were normalized by dividing by the mean of these outlined regions to produce "relative" values (rT2, rADC, rDWI, rCBF, rCBV, rMTT).

For the thresholding algorithms, tissue was classified as abnormal if the initial diffusion or perfusion values were greater than a specified number of standard deviations from the mean value measured in the contralateral non-infarcted gray matter regions. Tissue signature maps were generated using images calculated from the diffusion study (T$_2$+ADC+DWI), images calculated from the perfusion study (CBF+CBV+MTT), and combinations of images from both studies. For the combined study, signature maps were generated using combinations of T2 and ADC with one perfusion parameter (CBF, CBV or MTT) and all six parameters (T2+ADC+DWI+CBF+CBV+MTT). For creating signature maps, a threshold of 2 standard deviations from the mean of the contralateral values was used. Each of the resulting signatures was taken to represent a different "state" of infarction. Voxels not meeting any of the threshold criteria were given a "normal" signature. For the thresholding algorithms, which are based on an unsupervised approach not requiring training data from other subjects, the non-normalized datasets were used.

Using generalized linear model (GLM) algorithms, tissue outcome was modeled as a binary variable (infarcted/non-infarcted), P, where the value 1 represented infarcted tissue and value 0 non-infarcted tissue. In a GLM, for a binary variable, the probability of tissue infarcting can be represented by the logistic function recited below in Equation 2:

$$P = \frac{1}{1 + e^{-\eta(x)}} \qquad \text{Eq. (2)}$$

where $\eta(x)$, the predictor is a linear function of its input parameters, x, $\eta(x)=\beta^T x+\alpha$, $\beta$ is the vector of calculated coefficients and $\alpha$ is the bias or intercept term for the GLM. The $\alpha$ term provides the base value for P if all of the input parameters, x, are zero. The $\beta$ coefficients can be interpreted as the multiplicative effects on P due to changes in the input parameters.

In an exemplary embodiment, to calculate the coefficients in the GLM algorithms, a supervised approach was utilized. Using commercial image processing software (Alice, Hayden Image Processing Solutions, Boulder, Colo.), training regions were selected by outlining brain tissue volumes that were clearly infarcted or non-infarcted in the ipsilateral hemisphere in the coregistered follow-up axial T$_2$ FSE images by a neuroradiologist blinded to the predictive map results. Care was taken to avoid including regions demonstrating chronic changes on T$_2$, such as old stroke lesions or periventricular white matter abnormalities. Selection of normal voxels was also limited to the ipsilateral hemisphere in slices that showed evidence of infarction. Combinations of initial rT2 EPI, rADC, rDWI, rCBF, rCBV and rMTT values from these outlined training regions were used as the input vector, x, in the training stage. Because GLM algorithms assume independent observations, only every other voxel in the selected ROIs was sampled for the training data in order to reduce correlation. In one particular embodiment, the coefficients $\beta$ for the GLMs were calculated using an iterative reweighted least squares (IRLS) algorithm in software package S-PLUS 3.4 (StatSci, Seattle, Wash.).

Selection of covariates was based on the Akaike Information Criterion (AIC) whereby terms were included if their addition resulted in reductions in prediction error values that were a function of both training error and complexity. The AIC therefore provided an objective means to evaluate the trade-off between minimizing residual training error and complexity. The algorithm with the minimum AIC is therefore one with the minimum number of parameters and minimum training error. Automatic parameter selection was not utilized because all the input parameters were not independent with MTT=CBV/CBF and DWI=T$_2$ exp(−b ADC). Therefore, in selecting covariates, independent parameters, rT$_2$, rADC, rCBF and rCBV were considered first for inclusion followed by the higher order covariates of rDWI and rMTT. For purposes of comparing the two techniques, combinations of DWI and PWI identical to those created for the thresholding algorithms were generated for the GLM algorithms.

To validate the performance of the GLMs, a jack-knifing approach was followed wherein the coefficients for each patient's algorithms were calculated using the other patients in the study as training data. Jack-knifing was used to avoid bias that would otherwise occur if the algorithm's performance were evaluated on the same data that was used to train the algorithm. Using the calculated coefficients, the risk of a voxel of tissue going on to infarction was calculated as set forth above. Ninety-five percent confidence intervals for the computed risks were computed from the parameters obtained from the S-PLUS 3.4 software.

To evaluate the jack-knifing results for the GLM algorithms, the computed coefficients for each of the training datasets were compared to determine if they were significantly different (P>0.05) from the coefficients obtained using a dataset containing data from all patients. The average of the coefficients of the GLM algorithms obtained from the 14 training data subsets was also compared with the coefficients of the aggregate GLM algorithm. Two-tailed Z-tests were used for the statistical comparisons.

For evaluating the accuracy of the thresholding and GLM algorithms, the same infarcted and non-infarcted regions used in the training of the GLM algorithms were used. The performance of each of the algorithms was evaluated on its ability to accurately discriminate the infarcted from non-infarcted regions in the ipsilateral hemisphere. By comparing the predicted maps with lesions demonstrated on follow-up conventional MR images, the number of voxels predicted to infarct that actually did infarct (true positives or TP), and the number that did not infarct (false positives or FP) were tabulated. In addition, the number of voxels predicted not to infarct that remained non-infarcted (true negatives or TN) were tracked, as well as those that became infarcted (false negatives or FN).

From these counts, the algorithm's sensitivity or true positive ratio, TPR=TP/(TP+FN), and specificity or true negative ratio, TNR=TN/(TN+FP), were calculated. Receiver operating characteristic (ROC) curves were then generated for each algorithm by plotting TPR (sensitivity) against the false positive ratio (FPR) (1-specificity). For thresholding algorithms, the number of standard deviations was varied from −5 to 5 in 0.1 increments for all parameters except MTT. For MTT, cutoff values ranged from −10 to 10 standard deviations in 0.2 increments due to its relatively large range of values. For the GLM algorithms, the probability cutoffs for classifying tissue to be infarcted were varied from 0 to 1 in 0.01 increments.

The area under the ROC curves (AUC) represents the probability that an image will be correctly ranked normal or abnormal and therefore is used to assess the performance of diagnostic systems. The AUC for the ROC curves for each patient was calculated using numerical integration. The AUCs for the different algorithms were compared by paired one-tailed Wilcox on signed-rank tests. Values P>0.05 were considered significant in all statistical analysis. The performances of the algorithms were also compared at their optimal operating points (OOPs) on the ROC curves. As defined by Halpern, the OOP is the point where the ROC curve is tangent to the highest line of slope:

$$\frac{(\text{prevalence of disease})}{1 - (\text{prevalence of disease})} \times \frac{(\text{cost of false} - \text{positive result})}{(\text{cost of false} - \text{negative result})}$$

By assuming equal prevalence of infarcted (0.5) and non-infarcted (0.5) voxels and equal costs of false-positives and false-negatives, the OOPs for the ROC curves were determined numerically by finding the points on the ROC curves where the slope=1.

Based on the Akaike Information Criterion (AIC), GLM algorithms using different combinations of the possible six input parameters were evaluated and compared using data from all fourteen patients. Out of the independent parameters, rCBF resulted in the greatest reduction in the AIC, followed by $rT_2$, then rADC and finally rCBV. Adding the higher order terms, rDWI and rMTT resulted in a further reduction of AIC and were therefore included in the combined diffusion and perfusion GLMs. Therefore, the optimal GLM algorithm by the AIC requires all six parameters. However, for the purpose of comparison, the GLM coefficients for all possible 63 GLMs were calculated. A subset of these 63 GLMs that performed best in terms of sensitivity and specificity are shown in Table 1 below along with the standard errors for the estimates of each parameter, in which the columns labeled rT2, rADC, rDWI, rCBF, rCBV and rMTT represent the mean and standard error of the weighting coefficient for each respective parameter when utilizing all 14 patients for the training data set. The column labeled a is the bias or intercept term. Dashed lines indicate the parameter was not used for a particular multivariate algorithm. Each row represents the coefficients for the different GLM algorithms investigated.

The coefficients and intercepts for the aggregate GLM algorithm (Table 1) were not significantly different (P>0.5) from the mean of the coefficients across the 14 subjects. However, the coefficients and intercepts for some parameters in individual patients showed significant differences (P>0.05) from the aggregate GLM algorithm (Table 1) demonstrating the potential effects of training data on algorithm development.

For both approaches, the multivariate GLM algorithms performed better than the univariate GLM algorithms. Furthermore, GLM algorithms that combined diffusion and perfusion data performed better than the $rT_2$+rADC+rDWI or rCBF+rCBV+rMTT GLM algorithms as measured on higher ROC curves. The full six-parameter algorithm (T2+ADC+DWI and CBF+CBV+MTT) has a higher ROC curve than GLM algorithms using only $rT_2$+rADC+rMTT or $rT_2$+rADC+rCBF+rCBV parameters, consistent with the AIC results.

For the diffusion and perfusion based GLM algorithms, the multivariate algorithms provided the best performance in terms of ROC curves. Out of the combined algorithms, the algorithm using all six parameters provided the best performance. Algorithms using only perfusion imaging appear to have greater sensitivity in regions of low specificity (FPR>0.3). For algorithms using only diffusion imaging, the reverse appear true, that is the diffusion-based algorithm had greater sensitivity than perfusion-based algorithms in ranges of high specificity (FPR<0.3). When combining perfusion and diffusion information concurrently, an overall increase in sensitivity is obtained.

Table 2 below shows the specificities associated with the OOPs for both thresholding and GLM algorithms along with their corresponding sensitivities. The optimal operating points (OOPs) were determined for each of the evaluated algorithms. The cut-off values used for classification of infarcted and non-infarcted voxels that are associated with the OOPs are also shown. The cut-off values are in number of standard deviations for the thresholding algorithm for all parameters with the exception of MTT. The cut-off threshold of MTT was twice the standard deviations of the other five parameters. The cut-off values for the GLM algorithm are in percent risk of infarction. The third column and fourth represents the specificities and specificities at the OOPs for each of the algorithms.

TABLE 1

Coefficients of GLM algorithms for all 14 subjects.

| Algorithm | α | rT$_2$ | rADC | rDWI | rCBF | rCBV | rMTT |
|---|---|---|---|---|---|---|---|
| rT$_2$ + rADC + rDWI | −10.0 ± 0.2 | −2.9 ± 0.2 | 4.9 ± 0.2 | 6.7 ± 0.2 | — | — | — |
| rCBF + rCBV + rMTT | −1.2 ± 0.06 | — | — | — | −1.2 ± 0.09 | −0.02 ± 0.06 | 0.6 ± 0.03 |
| rT$_2$ + rADC + rMTT | −3.6 ± 0.06 | 4.4 ± 0.08 | −3.5 ± 0.07 | — | — | — | 0.9 ± 0.02 |
| rT$_2$ + rADC + rCBF + rCBV | −1.6 ± 0.05 | 4.4 ± 0.08 | −3.3 ± 0.07 | — | −3.0 ± 0.06 | 1.2 ± 0.04 | — |
| Combined Algorithm | −11.7 ± 0.2 | −3.0 ± 0.2 | 5.9 ± 0.2 | 7.1 ± 0.2 | −1.2 ± 0.1 | 0.05 ± 0.06 | 0.7 ± 0.03 |

TABLE 2

Optimal operating points for thresholding and GLM algorithms.

| Algorithm | Cut-off Values | Specificity | Sensitivity |
| --- | --- | --- | --- |
| Thresholding | | | |
| T2 + ADC + DWI | 2.2 | 0.87 | 0.54 |
| CBF + CBV + MTT | 1.6 | 0.64 | 0.72 |
| Combined Algorithm | 2.7 | 0.83 | 0.66 |
| GLM | | | |
| T2 + ADC + DWI | 34 | 0.90 | 0.50 |
| CBF + CBV + MTT | 28 | 0.65 | 0.71 |
| Combined Algorithm | 32 | 0.84 | 0.66 |

The OOPs are comparable for both thresholding and GLM algorithms. For both algorithms, from the ROC curves shown in FIG. 2, the "combined algorithms" have the greatest sensitivities at each of the specificities listed in Table 2.

Both thresholding and GLM methods produce similar ROC curves when pooling results across the fourteen subjects. ROC curves were also generated on an individual patient basis and the area under the curves (AUC) calculated. The differences between the multivariate algorithms' AUCs were calculated for the thresholding and GLM algorithms. For the thresholding algorithm, the combined algorithm had significantly higher AUCs than the diffusion-based algorithm (T2+ADC+DWI) (P=0.02) indicating better overall performance of the combined threshold algorithm over the initially proposed diffusion-only thresholding algorithm.

The difference between the "Combined Algorithm" and CBF+CBV+MTT threshold algorithms were not significant (P=0.21). No significant difference was found between the performances of threshold algorithms based purely on diffusion (T2+ADC+DVI) and those based purely on perfusion (CBF+CBV+MTT) (P=0.52). For the GLM algorithms, the "Combined Algorithm" showed a significant improvement over diffusion based algorithms (rT2+rADC+rDWI) (P=0.02) and perfusion based algorithms (rCBF+rCBV+ rMTT) (P=0.04). There was no significant difference between multivariate diffusion and multivariate perfusion GLM algorithms (P=0.50).

The lack of difference between the diffusion and perfusion algorithms for both GLM and thresholding algorithms is most likely because diffusion algorithms have lower sensitivity at low specificity than perfusion algorithms but higher sensitivity at high specificity which may in turn translate into equivalent AUCs.

Differences between the AUCs for the GLM algorithms and their corresponding threshold algorithm counterparts were calculated and compared. The GLM and thresholding algorithms using diffusion data (P=0.33), perfusion data (P=0.64) or combined algorithms (P=0.27) performed comparably.

Referring again to FIG. 1, acute imaging studies and thresholding maps for a 45 year-old male stroke patient imaged within 7 hours of symptom onset are shown. The tissue signature maps are the results of using only hyperacute diffusion data (T2+ADC+DWI), hyperacute perfusion data (CBF+CBV+MTT) and combining all six input parameters ("Combined Algorithm"). The diffusion-based algorithm, though identifying a smaller region at risk of infarction in the ipsilateral hemisphere than either the perfusion-based algorithm or "Combined Algorithm", also demonstrates an abnormal signature in the contralateral hemisphere. Abnormal tissue signatures in the perfusion-based algorithm are predominantly limited to the ipsilateral hemisphere although they encompass an area much greater than the follow-up infarct volume. Because misclassifications are cumulative in the thresholding algorithms, the results in the combined diffusion and perfusion algorithms have similarly high sensitivity but poor specificity as that shown for the perfusion based algorithms. However, a greater number of tissue states exist in the combined algorithm resulting in greater heterogeneity than those based on algorithms incorporating only diffusion or perfusion information.

Figure 2:
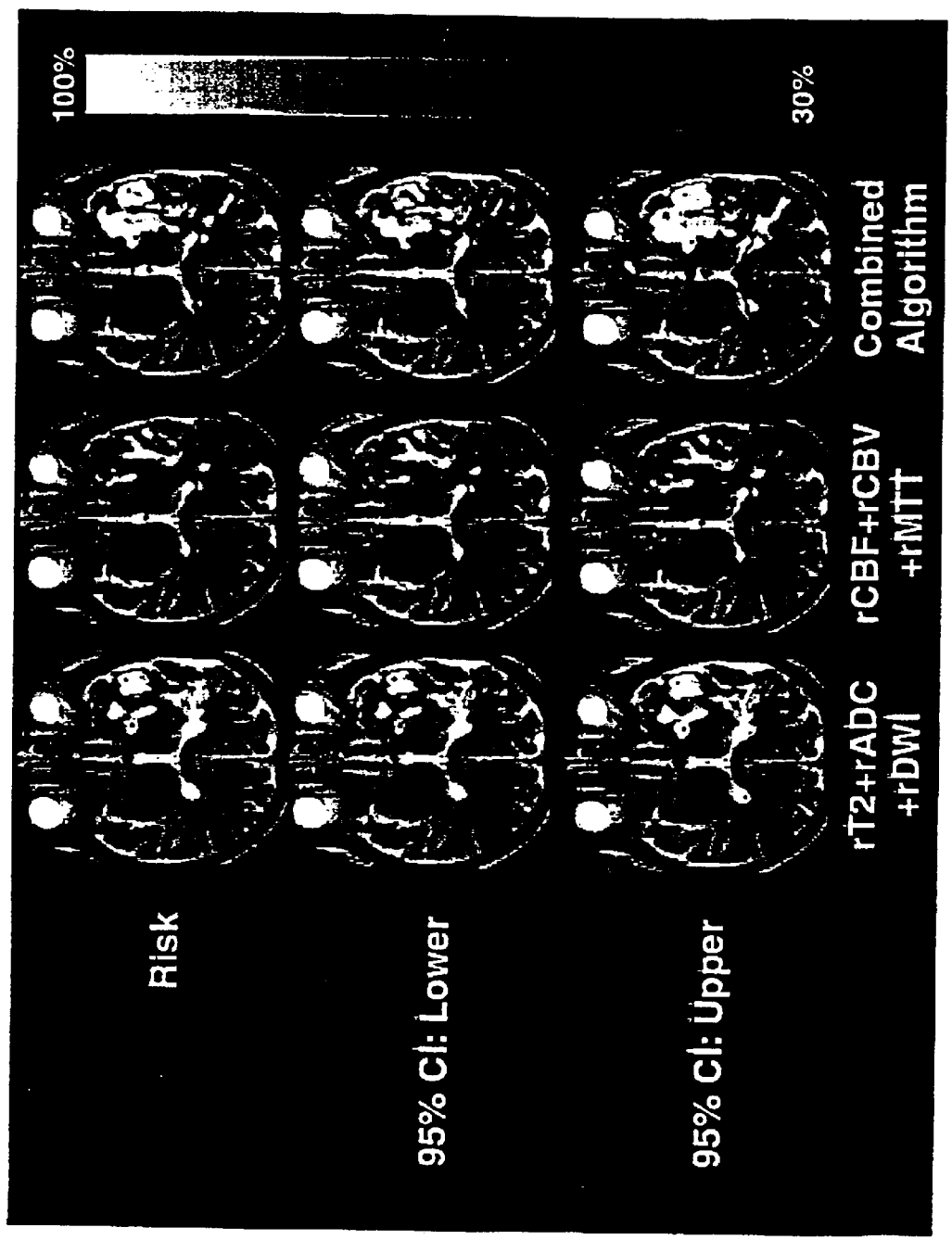
FIG. 2 shows risk maps for the patient whose acute data is shown in FIG. 1 overlaid on a two-month follow-up imaging study with confidence intervals for the infarction predictions.

FIG. 2 shows the results of the GLM algorithms using the same imaging data as shown in FIG. 1. The algorithms utilizing diffusion alone (rT2+rADC+rDWI) underestimate the follow-up infarct volume. Maps using only perfusion information (rCBF+rCBV+rMTT) overestimate the follow-up infarct volume. The "Combined Algorithm", however, predicts an area at high risk of infarction, as evidenced by the red-yellow region, that correlates well with the follow-up lesion areas as demonstrated on the two month follow-up T2 FSE image. In addition, for all algorithms, the regions predicted to be at high risk of infarction are predominantly localized to the ipsilateral hemisphere as compared to the results of the thresholding algorithm.

Figure 3:
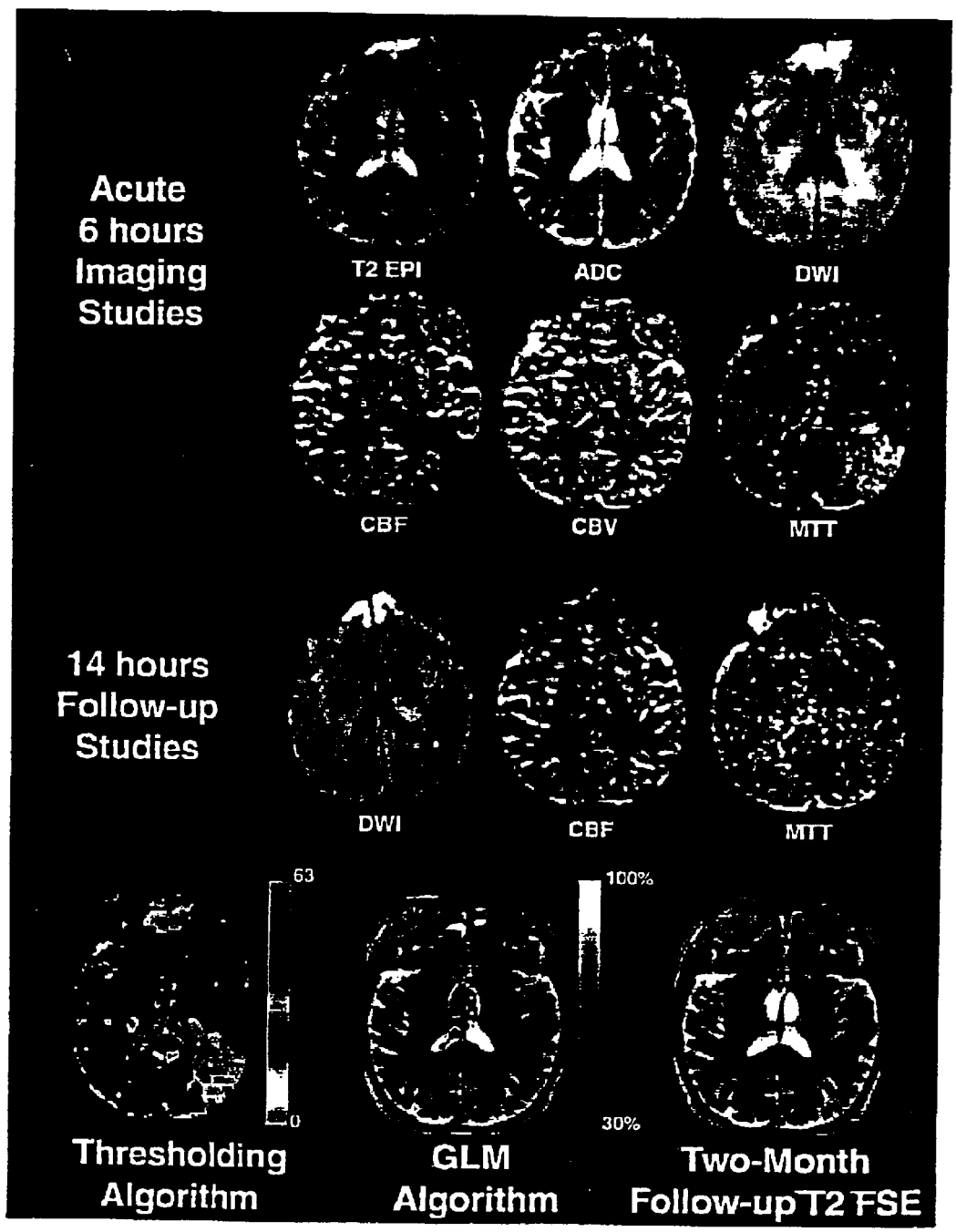
FIG. 3 is a further series of acute image data for a stroke patient who spontaneously reperfused as demonstrated by the imaging study taken 8 hours later.

The results of applying the statistical algorithms to a patient with early reperfusion as defined by follow-up perfusion studies are shown in FIG. 3. The acute MRI studies for Patient 11 appear normal with the exception of decreased CBF and increased MTT in the left temporo-parietal lobe. The imaging study eight hours later show a slight diffusion abnormality in the area shown abnormal in the initial perfusion study. However, the remaining perfusion defects appear to have resolved as demonstrated by the CBF and MTT maps, suggesting the occurrence of spontaneous reperfusion. Both the thresholding and the GLM based risk maps over predict the follow-up infarct volume in the two-month follow-up T2 FSE. The resolution of much of the abnormalities in the follow-up imaging study was consistent with the patient's improved clinical outcome.

Thus, a voxel-by-voxel risk map can be generated to provide quantitative predictive maps of tissue outcome utilizing acute MRI images. By extending tissue signature algorithms based on thresholding to include perfusion information, the results show that such inclusion improves the predictive power of signature maps. GLM algorithms provide the risk of the tissue infarcting as a continuous variable that ranges between 0 and 1 and therefore, as stroke evolves, the risk of individual voxels of tissue can be monitored quantitatively by a single variable. The recruitment of voxels in the presumed "ischemic penumbra" might therefore be quantified as the change in risk in the peripheral areas from low probability to high probability over time.

The algorithms have been trained on data from patients who did not receive thrombolytic or neuroprotective therapy. The two patients with spontaneous reperfusion were specifically not excluded from the training set since their inclusion were believed to be a better reflection of the naturally occurring ischemic stroke patient population where spontaneous reperfusion has been detected within 24 hours after symptom onset in 24% of patients using transcranial doppler ultrasound. Therefore, the algorithms' predictions seem likely to be based on the natural evolution of ischemic tissue undergoing infarction. It is understood, however, that the exemplary training set described herein is relatively small, and therefore does not yet capture the full range and frequency of stroke evolution possibilities. For example, if in a new patient an event occurs to interrupt the progression of ischemic damage as quantified from the training patient data, the probability of infarction of individual tissue regions may change greatly. This was apparent in the case shown in FIG. 3, which showed spontaneous reperfusion. For such circumstances progression of infarct lesion size have been shown to be diminished.

At their optimal operating points, thresholding algorithms combining DWI/PWI provided 66% sensitivity and 83% specificity and GLM algorithms combining DWI/PWI predicted with 66% sensitivity and 84% specificity voxels that proceeded to infarct. Thresholding algorithms combining DWI/PWI provided significant improvement over algorithms that utilized DWI alone (P=0.02) but no significant improvement over algorithms utilizing PWI alone (P=0.21). GLM algorithms combining DWI/PWI showed significant improvement over algorithms using only DWI (P=0.02) or PWI (P=0.04). The performances of thresholding and GLM algorithms were comparable (P>0.2).

EXAMPLE 2

Sixty-six patients were entered into a phase I/II trial of basic fibroblast growth factor (bFGF), FIBLAST. This trial was a double-blind, randomized, placebo-controlled, dose-escalation, and three month follow-up study of intravenous infusion of basic fibroblast growth factor (bFGF). Patients were randomized either to placebo or one of six different doses of bFGF ranging from 9 to 150 µg/kg. Eleven patients were enrolled at Massachusetts General Hospital (MGH). Each patient underwent MRI imaging according to the standard MGH protocol within the first ten hours of symptom onset, and follow-up imaging at discharge.

Diffusion and perfusion MR imaging were performed using published MGH imaging protocol and techniques. Diffusion weighted imaging (DWI) included full-tensor imaging at a b-value of 1221 s/mm$^2$, over a volume of 18 slices, TR=6 s, TE=118 ms, 6 mm thick slices, 1 mm interslice gap, 256×128 in-plane resolution over a 40×20 cm field of view.

Perfusion weighted images (PWI) were acquired over 10–11 slices at TR=1.5 s using either spin-echo (SE) EPI at TE=75 ms or gradient-echo (GE) EPI at TE=50 ms and flip angle=90° during the first pass of a bolus of 0.1 (GE) or 0.2 (SE) mmol/kg of a gadolinium-based contrast. The in-plane resolution of all images were 1.56×1.56 mm$^2$ with a slice thickness of 6 mm and a 1 mm interslice gap. From these images, relative cerebral blood volume (rCBV), relative cerebral blood flow (rCBF) and mean transit time (MTT) maps were then computed on a voxel-by-voxel basis using techniques well known to one of ordinary skill in the art.

Conventional MR images were also obtained, which included axial T2 fast spin echo (FSE) and fluid attenuated inversion recovery (FLAIR) images, as well as 2D phase contrast MR angiography and sagittal T1 weighted images. Each patient also underwent CT scanning prior to entering the study.

A generalized linear model (GLM) of risk of tissue infarction was generated from retrospective studies of hyperacute cerebral ischemia patients who received diffusion and perfusion weighted imaging within twelve hours of presenting with symptoms. Only patients with cortical infarcts caused by occlusion of major cerebral arteries were included in the training data. Patients were excluded if they received novel therapeutic treatments or if there did not exist at least a five day follow-up study to confirm the extent of the infarct. This resulted in a total of fourteen patients for the training data set. The volumetric diffusion and perfusion data were coregistered utilizing an automated image registration software package (AIR 3.08). Utilizing a supervised learning algorithm and logistic regression, the parameters for the GLM were computed using coregistered data sets, as described in the previous section.

Figure 4:
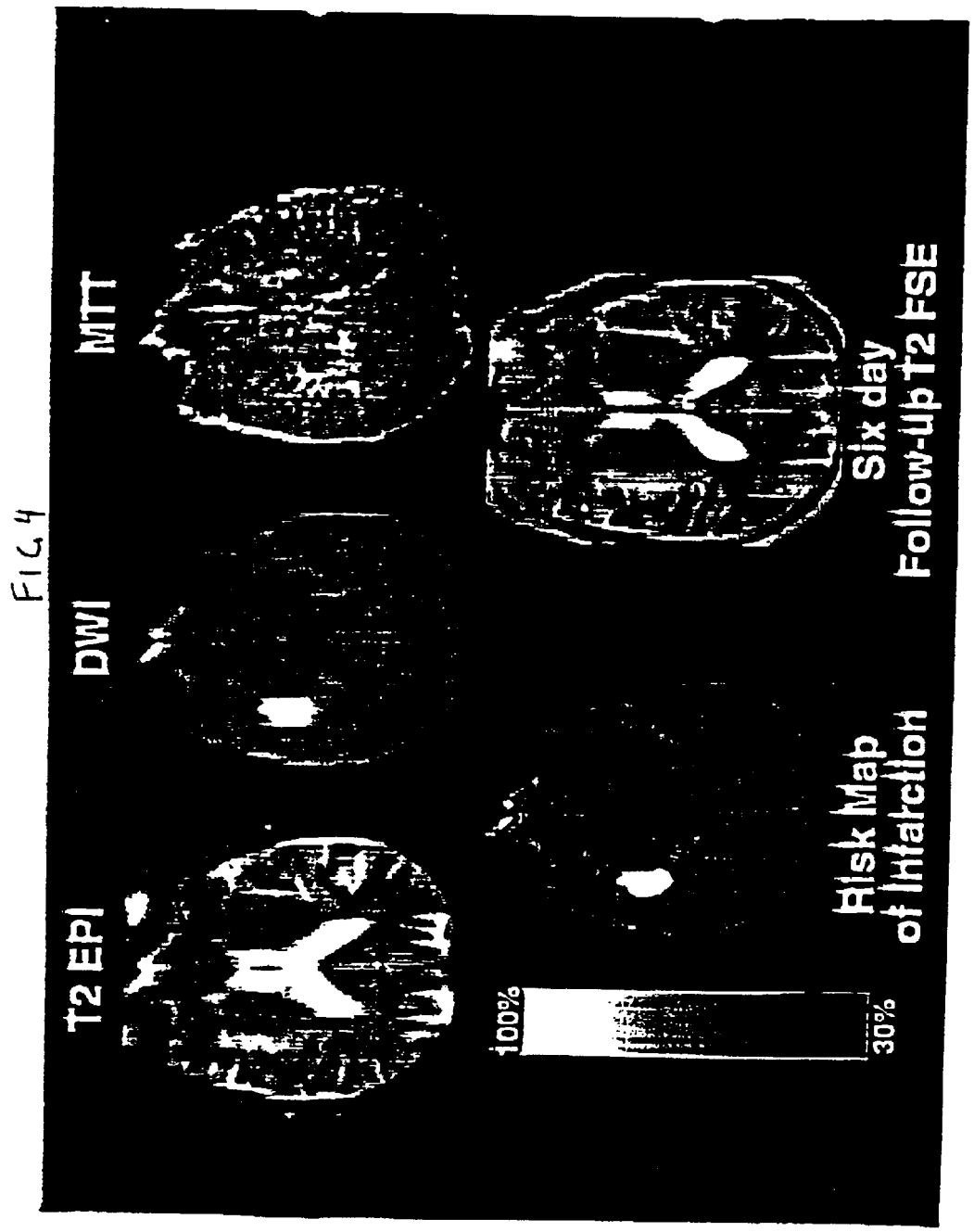
FIG. 4 is another series of acute image data for a stroke patient receiving placebo enrolled in a trial of basic fibrinogen growth factor (bFGF.

An example input and corresponding output is shown in FIG. 4 demonstrating the good correlation between areas predicted to go on to infarct and final infarct volume as confirmed in the follow-up T2 FLAIR. In one embodiment, a GLM algorithm is used to model tissue outcome. Tissue outcome y can be modeled as a binary variable (normal/abnormal) and therefore a Bernoulli probability density function assumed for its distribution. The logistic function can then be used to compute y as set forth below in Equation 1:

$$y = \frac{1}{1 + e^{-\beta x}} \qquad \text{Eq. (1)}$$

where y is an estimate of the risk of infarction, x represents an input vector that can include an initial T2, ADC, rCBF (relative cerebral blood flow), rCBV (relative cerebral blood volume) and MTT (mean transmit time) data and B the calculated coefficients.

The primary efficacy measure was change in NIH Stroke Scale (NIHSS) score measured at admission compared to that reported at discharge. Patients were classified as having an improved outcome if the NIH SS score decreased by more than four points. Two by two contingency tables were computed for the placebo versus the bFGF treated patients and a Fisher's Exact test performed.

The dose of bFGF was correlated with the positive predictive value (PPV) of the GLM model described in the previous section. Four of the eleven patients were excluded due to incomplete DWI and PWI data sets. Maps of the risk of infarction for the seven remaining patients were generated utilizing coregistered initial DWI and PWI data sets. Voxels were classified as going on to infarction if their risk were greater than a specified threshold. The PPV of the model was computed for each patient by comparing predicted infarct volume with final infarct volume at time of discharge. Final lesion regions of interest for performance evaluation were selected by a neuroradiologist using a semi-automated image processing software (Alice). Matching normal ipsilateral regions were also selected. The number of voxels that was correctly predicted to go on to infarction (true positives or TP) were computed as well as the number that were incorrectly predicted to go on to infarction (false positives or FP). The PPV was obtained by taking the ratio of TP/(TP+FP).

Table 3 below shows the initial and final scores NIHSS for each of the 11 patients enrolled at MGH. Table 3: Scores on the NIHSS at admission and at discharge.

| Patient | Initial Scan (hrs:mins) | NIH SS (Initial) | Follow-up (days) | NIH SS (Discharge) | Dosage (µg/kg) |
| --- | --- | --- | --- | --- | --- |
| 1 | 8:50 | 4 | 5 | 2 | Placebo |
| 2 | 8:35 | 9 | 6 | 2 | Placebo |
| 3 | 7:45 | 15 | 7 | 5 | 9 |
| 4 | 9:15 | 15 | 7 | 11 | 27 |
| 5 | 5:35 | 6 | 4 | 1 | 75 |

-continued

| Patient | Initial Scan (hrs:mins) | NIH SS (Initial) | Follow-up (days) | NIH SS (Discharge) | Dosage (µg/kg) |
|---|---|---|---|---|---|
| 6 | 6:35 | 16 | 13 | 14 | 150 |
| 7 | 7:50 | 17 | 19 | 12 | 150 |
| 8* | 5:45 | 4 | 8 | 2 | 75 |
| 9* | 2:20 | 2 | 3 | 2 | 3 |
| 10* | 5:20 | 4 | 5 | 3 | 75 |
| 11* | 9:00 | 18 | 7 | 20 | 3 |

*Incomplete initial MRI data sets

Patients with greater than a four point change on the NIH SS score were classified as having a favorable outcome. A 2×2 contingency table, shown in Table 4, was evaluated for statistical independence between treated and placebo groups using Fisher's exact test.

TABLE 4

2 × 2 Contingency table based on improved outcome

|  | ΔNIH SS ≧ 4 | ΔNIH SS < 4 |
|---|---|---|
| Treated | 4 | 4 |
| Placebo | 1 | 2 |

No statistical significance was found. Similar analysis was performed for the subset of 7 patients who were evaluated with GLM models. The contingency table is shown in Table 5.

TABLE 5

2 × 2 Contingency table based on improved outcome for subset of 7 patients

|  | ΔNIH SS ≧ 4 | ΔNIH SS < 4 |
|---|---|---|
| Treated | 4 | 1 |
| Placebo | 1 | 1 |

No statistical significance was found for this subset as well.

Figure 5:
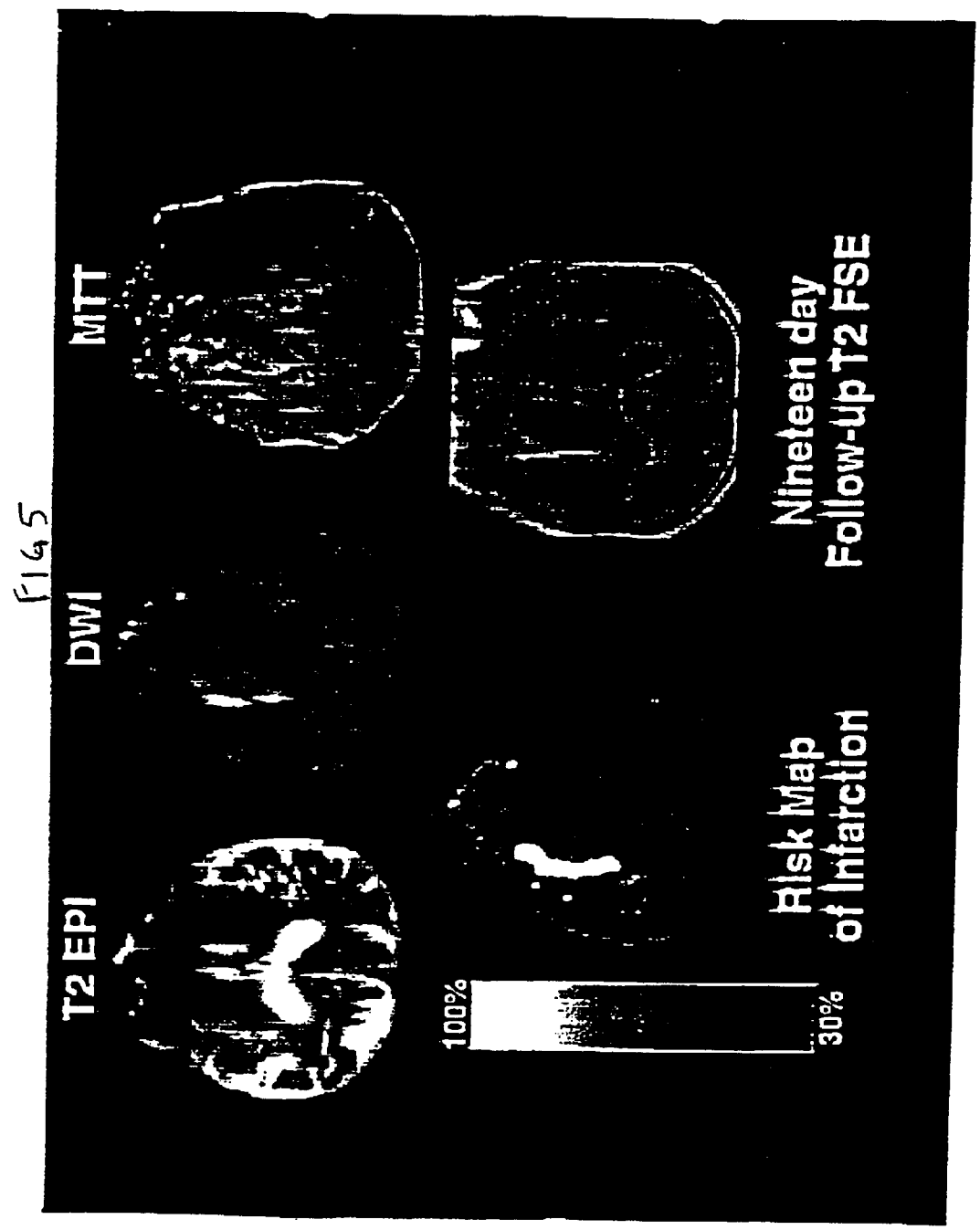
FIG. 5 is another series of acute image data for a stroke patient enrolled in the bFGF trial receiving the full dose (150 ug/kg) of bFGF.

FIG. 5 shows an example predicted risk map of infarction for Patient 7. The scale is probability of infarction. The top row shows the input data to the model. The bottom row shows the predicted map overlaid on the initial DWI image. One sees from the image that the area at high risk of infarction correlates to the initial DWI abnormality. However, the penumbra surrounding the core represents an area at risk of infarction that does not go on to infarction as demonstrated in the 19 day follow-up FLAIR. Patient 7 had been randomized to receive the full-dose of bFGF. In this case, the GLM provided a poor positive predictive capability.

The generated risk maps can be used to evaluate and/or select novel stroke treatments, as described below in detail. In general, a risk threshold is selected to facilitate evaluation of a novel treatment, such as a drug. The risk threshold can be selected to determine tissue at greatest risk of infarction if treated with a conventional therapy. The risk threshold can also be selected to determine a treatment option from a plurality of treatment options based upon volume reduction of tissue above a specified risk and/or reduction of risk value.

Figure 6:
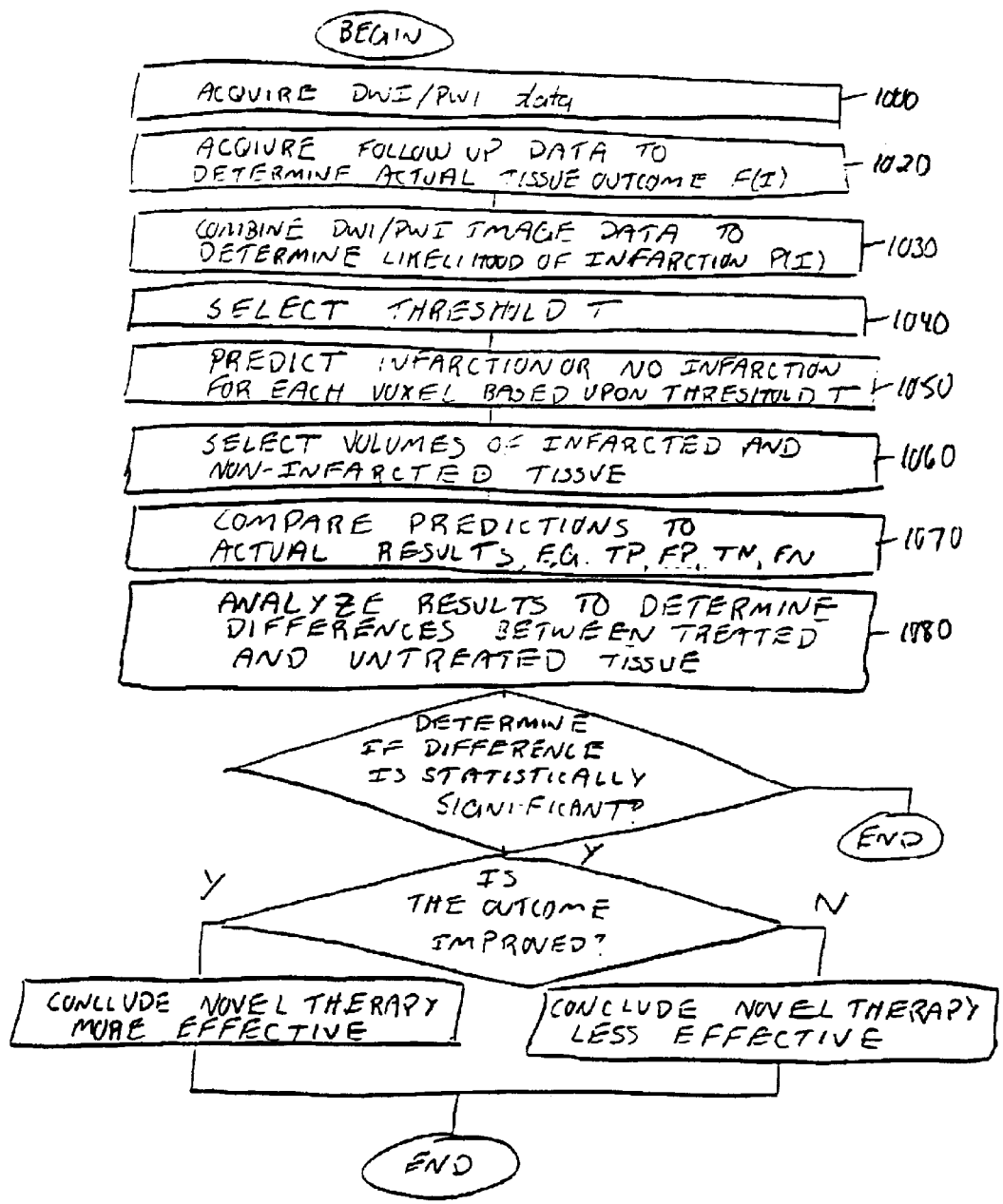
FIG. 6 is a flow diagram of an exemplary sequence of steps for evaluating a novel treatment with a risk map in accordance with a present invention.

FIG. 6 shows an exemplary sequence of steps for evaluating a novel therapy in accordance with the present invention. In step 1000, prospective DWI and PWI data, which is also referred to as acute MRI data, is acquired from acute stroke patients prior or immediately post-treatment. Included in such data is placebo-treated or control patients acquired as part of a clinical trial, for example. In step 1020, follow-up conventional studies are acquired as a gold standard to determine the tissue's true outcome, F(I), e.g., infarcted or not-infarcted for each individual voxel, I. Conventional studies may include CT or MR, which can be coregistered with the acute MR studies.

In step 1030, the acute MRI data is processed using an algorithm to combine the DWI and PWI data to generate a risk map. In one embodiment, a GLM predictor is used to generate maps of the likelihood of infarction, P(I) on a voxel-by-voxel basis, as described above. This estimate, P(I), is a continuous probability variable whose value ranges between 0 and 100%, where higher values represent higher risks of infarction.

In step 1040, depending on the target therapy, a threshold T is selected to determine which tissue is at greatest risk of infarction if the patient receives conventional therapy. In one particular embodiment, a threshold T of thirty percent is selected. In general, the threshold is selected to obtain the optimal operating point for discriminating tissue likely to infarct from tissue not likely to infarct for patients receiving a conventional therapy. For example, to demonstrate an improvement in patients treated with a novel therapy over conventional therapy, a threshold of 30% may be used. Alternatively, the threshold T may change in patients receiving treatment specifically targeted at high risk regions, e.g. >80%, or low risk regions (<20–40%).

The selection of the threshold T is dependent upon the application. This might be done in a jack-knifing fashion, or using a predetermined subset (such as the first third of the subjects) to select the optimal threshold, T. The latter approach would include deciding on a relevant distinction, such as clinical outcome or treated versus untreated status. Then, the range of threshold values that best statistically separated treated versus untreated groups could be computed on the subset of data.

In step 1050, the selected threshold value T is then used for evaluating the data. In one embodiment, if the risk of infarction P(I) is greater than the threshold, i.e., P(I)>T, the tissue is predicted to infarct (f(I)=infarcted). Otherwise the tissue is predicted to not infarct (f(I)=not-infarcted).

In step 1060, volumes of infarcted and non-infarcted tissue are selected. For example, using coregistered follow-up images, volumes of infarcted tissue, and non-infarcted tissue are outlined in the ipsilateral hemisphere. In one particular embodiment, the ipsilateral hemisphere is selected as the volume to select voxels since that would be typically the area at greatest risk of infarction. The voxels are limited to these areas in order to prevent biasing the results to great accuracy than achieved due to the plethora of normal voxels in the contralateral hemisphere. However, if a treatment is targeted to both hemispheres, the user can opt to evaluate both hemispheres since the models can generate risks of infarction for the entire brain.

Figure 7:
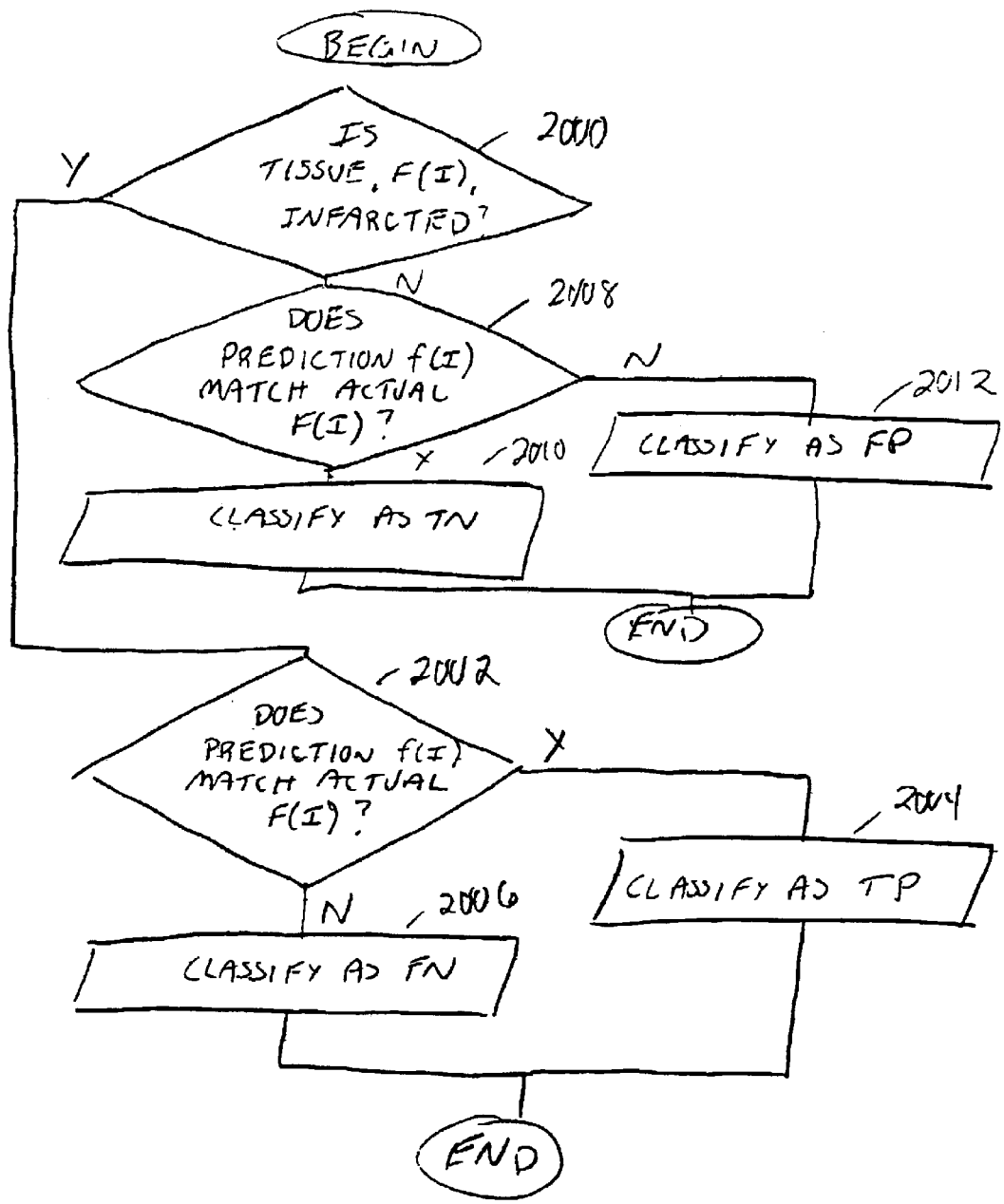
FIG. 7 is a flow diagram showing further details of evaluating a novel stroke treatment in accordance with the present invention.

In step 1070, the voxel predictions, f(I) are compared with actual results, F(I). Referring briefly to FIG. 7, one technique for comparing the results includes estimating the accuracy of the prediction by calculating the number of true positives (TP), false positives (FP), true negatives (TN) and false negatives (FN). In step 2000, it is determined whether the tissue F(I) is infarcted based upon follow up imaging. If so, in step 2002 the prediction is compared to the actual tissue condition. If the tissue state matches the predicted tissue state, the voxel is classified at true positive TP in step 2004. If the prediction does not match, then in step 2006 the voxel is classified as false negative FN. If the tissue is not infarcted, as determined in step 2000, the prediction is compared to the actual tissue state in step 2008. The voxel is then classified as true negative TN in step 2010 if the prediction matches or as false positive FP in step 2012.

Referring again to FIG. 6, in step 1080 the results can be analyzed to determine if a statistically significant difference exists between treated and untreated (control group) patients. For example, taking combinations of these parameters, e.g. a positive predictive value (PPV=TP/(TP+FP), the performance of models for placebo patients and treated patients can be compared. If there is a significant difference between the two patient populations, it can be assumed that the treatment either improves patient outcome (e.g., treated patients have more false positives) or worsens outcome (e.g., treated patients have more false negatives). If no significant difference is found, then efficacy of the novel treatment cannot be shown. If the clinical trial is a dose ranging study, this technique is still applicable since PPV can be plotted as a function of dose. That is, if a drug is effective as a function of dose, the ability of the model to predict which voxels infarct should decrease as dose increases.

Figure 8:
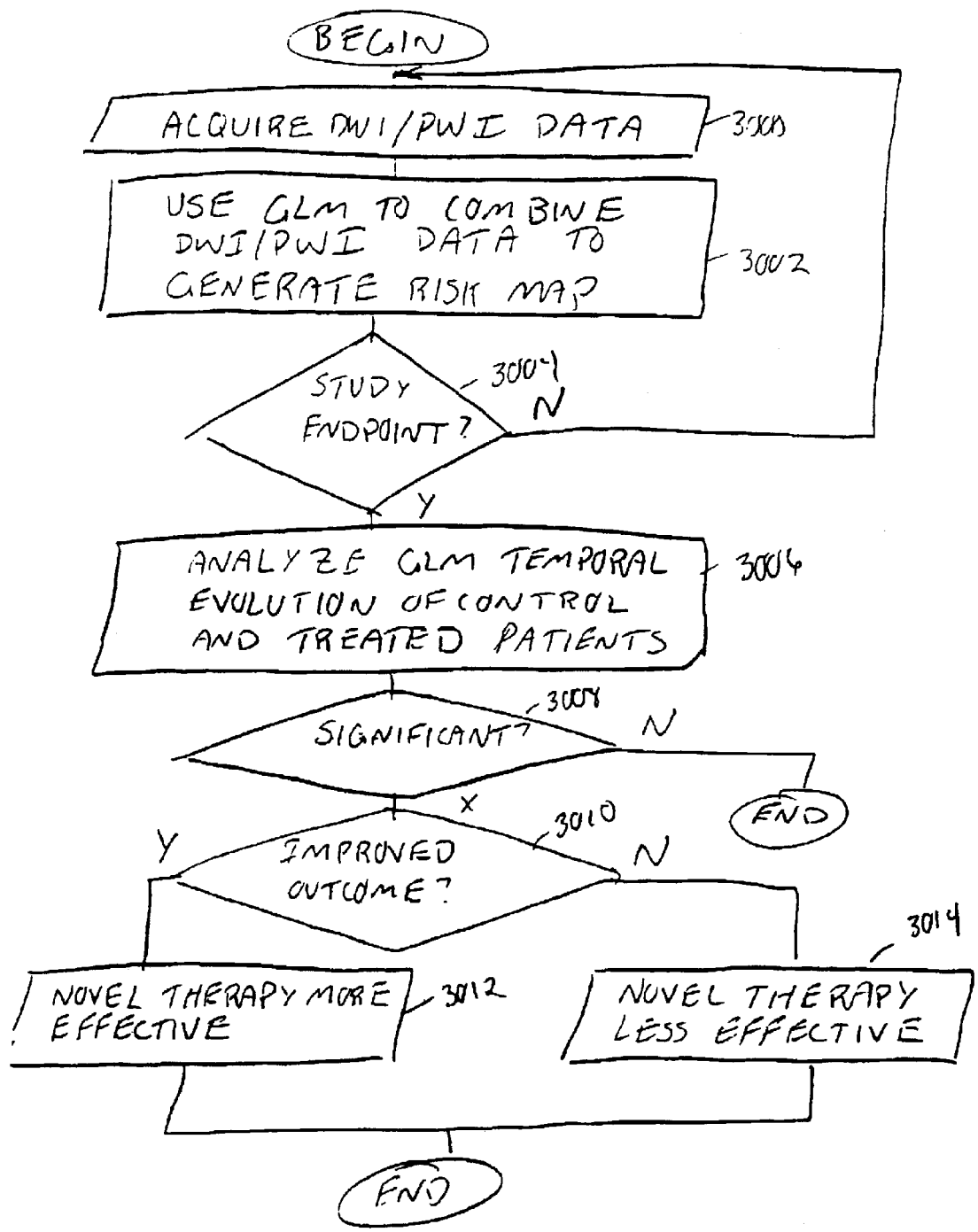
FIG. 8 is a flow diagram of an exemplary sequence of steps for evaluating stroke treatment in accordance with the present invention.

FIG. 8 shows another embodiment of evaluating novel treatments with a risk map in accordance with the present invention. In one particular embodiment, a risk map is generated using a GLM algorithm to evaluate the efficacy of a novel treatment. In step 3000, patient DWI and PWI data is acquired at predetermined intervals. In step 3002, the DWI and PWI data is combined, such as by using a GLM or GAM, to generate risk maps from the acquired data. After the study endpoint, which is determined in step 3004, the temporal evolution of treated and untreated patients is analyzed in step 3006. More particularly, if a therapy was effective, the patient's risk of infarction should decrease over time on a voxel-by-voxel basis. However, a placebo patient's risk will increase over time. In this application, a statistical comparison of evolution of risk values in tissue in treated patients as compared to placebo patients can be plotted. In step 3008, it is determined whether there is a statistically significant result. If so, in step 3010 it is determined whether patient outcome improved to make a determination that the novel treatment is effective in step 3012 or a determination that the novel treatment is not effective in step 3014.

Figure 9:
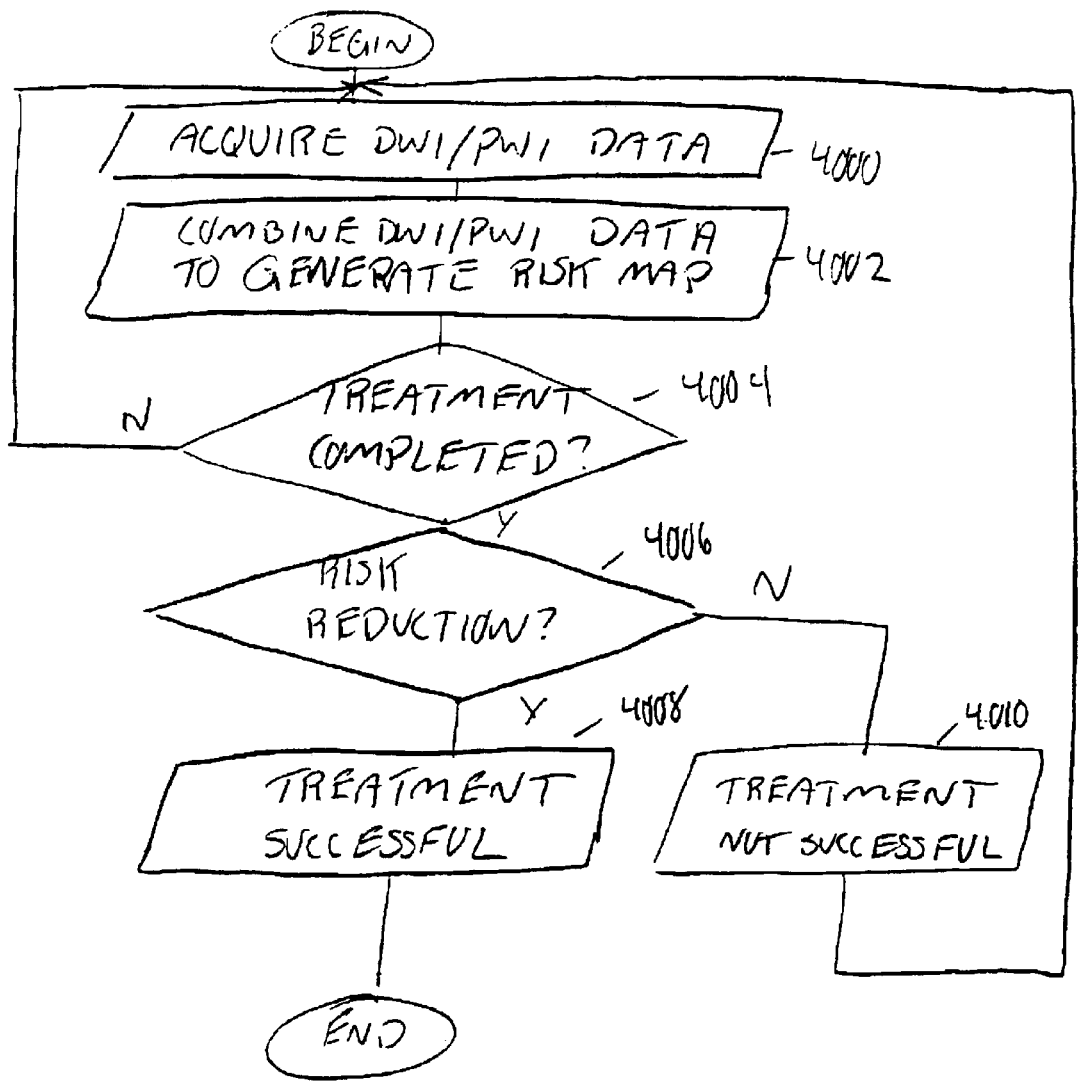
FIG. 9 is a further flow diagram for evaluating novel stroke treatment in accordance with the present invention.

For treatment planning, as shown in FIG. 9, risk maps can be assessed to determine the efficacy of one treatment and still allow the clinician the option to switch to an alternate treatment. The efficacy assessment can be done either by volume reduction of tissue at risk greater than a certain threshold or in quantitative terms as a reduction of the risk values themselves as a measurable value. In one particular embodiment, in step 4000, patient DWI and PWI data is acquired to generate a risk map in step 4002. After completion of the treatment, as determined in step 4004, it is determined whether the novel treatment has reduced risk of tissue infarction in step 4006. If so, the treatment is determined to be successful in step 4008. If not, the treatment is considered to be unsuccessful in step 4010.

Figure 10:
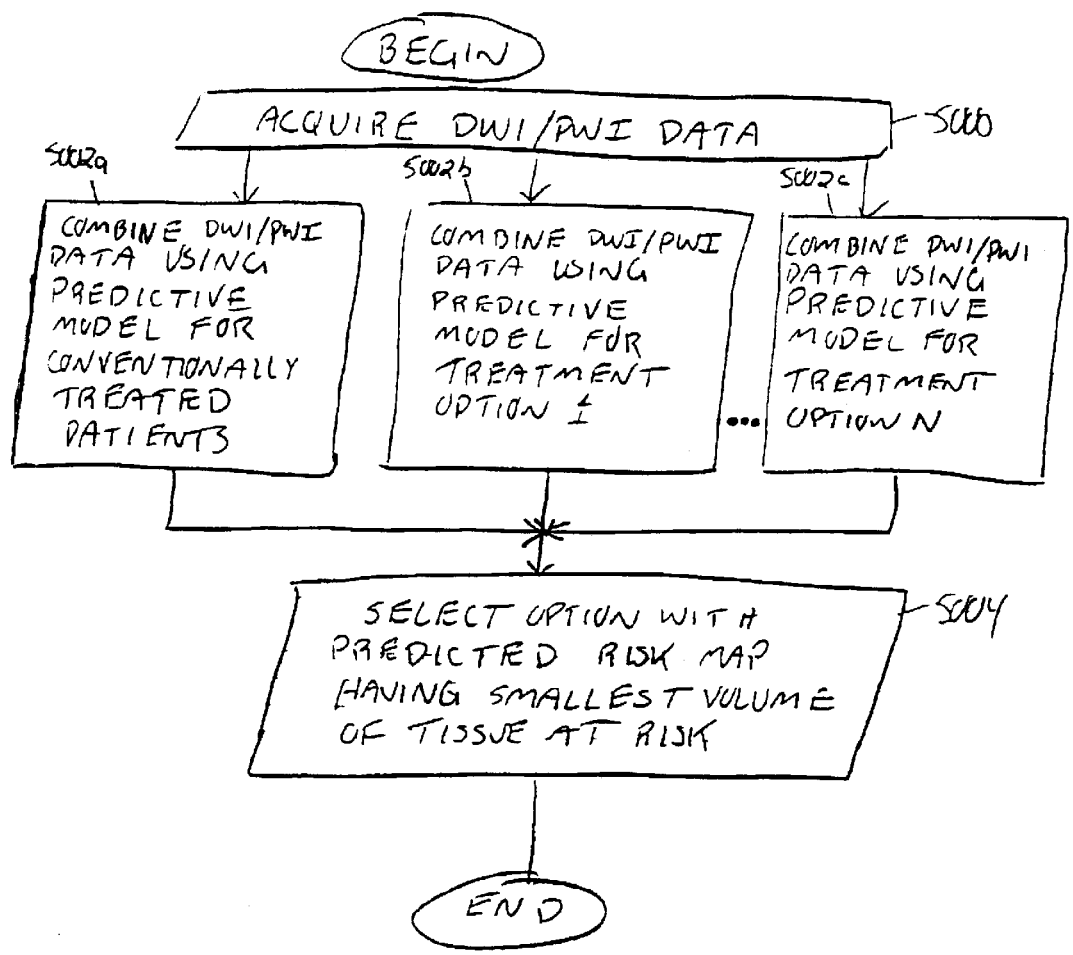
FIG. 10 is a flow diagram of an exemplary sequence of steps for selecting a novel stroke treatment in accordance with the present invention.

FIG. 10 shows another embodiment utilizing a risk map as a guide for treatment planning. In step 5000, acutely acquired MRI data will be analyzed using models trained with data from N different treatments. That is, in step 5002*a*, the DWI/PWI data is combined using a predictive model for conventionally treated patients. In step 5002*b*, data is combined to generate a risk map for a first treatment option. And in step 5002*c*, data is combined to generate a risk map for treatment option N. In step 5004, the treatment option having a risk map with the smallest volume of tissue at risk of infarction is selected. Alternatively, the treatment option that minimizes the risk, e.g. 30% instead of 80%, can be selected.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of evaluating a novel stroke treatment, comprising:
   generating a risk map indicating voxel-by-voxel statistical probability of tissue infarction;
   selecting a probability risk threshold for tissue infarction risk in the risk map;
   evaluating the therapeutic effect of the novel stroke treatment by comparing the selected probability risk threshold and actual tissue infarction state on a voxel-by-voxel basis.

2. The method according to claim 1, further including combining DWI and PWI data to generate the risk map.

3. The method according to claim 2, wherein the DWI data is selected from one or more types selected from the group consisting of elements of the diffusion tensor such as ADC, low-b EPI T2 image, anisotropy indices, eigenvalues and eigenvectors.

4. The method according to claim 2, wherein the PWI data is selected from one or more types selected from the group consisting of CBF, CBV, MTT and other parameters of the dynamic susceptibility contrast-enhanced images.

5. The method according to claim 2, wherein the risk map is generated using a GLM algorithm combining EPI T2, ADC, DWI, CBF, CBV, and/or MTT data.

6. The method according to claim 1, further including utilizing a GLM algorithm to generate the risk map.

7. The method according to claim 1, further including utilizing a GAM algorithm to generate the risk map.

8. The method according to claim 1, further including determining whether the novel treatment achieves a statically significant difference as compared to a conventional therapy.

9. The method according to claim 8, further including determining whether the novel therapy is effective.

10. The method according to claim 1, further including calculating true positive, true negative, false positive, and false negative values.

11. The method according to claim 1, further including generating a plurality of risk maps, each of which corresponds to a particular therapy.

12. The method according to claim 11, further including selecting one of the plurality of therapy based upon the plurality of risk maps.

13. The method according to claim 12, further including selecting a therapy corresponding to a respective one of the plurality of risk maps having a smallest volume of tissue risk of infarction.

14. The method according to claim 12, further including selecting a therapy corresponding to a respective one of the plurality of risk maps that minimizes a risk threshold of infarction.

15. The method according to claim 1, further including selecting the risk threshold based upon which tissue is likely to infarct if a patient receives conventional therapy.

16. The method according to claim 1, further including selecting the risk threshold based upon an optimal operating point for discriminating tissue likely to infarct front tissue not likely to infarct.

17. The method according to claim 1, further including selecting the risk threshold of about thirty percent.

18. The method according to claim 1, further including selecting the risk threshold based upon a risk level of tissue targeted by the novel treatment.

* * * * *

UNITED STATES PATENT AND TRADEMARK OFFICE
CERTIFICATE OF CORRECTION

PATENT NO. : 7,020,578 B2
APPLICATION NO. : 10/182978
DATED : March 28, 2006
INVENTOR(S) : Sorenson et al.

It is certified that error appears in the above-identified patent and that said Letters Patent is hereby corrected as shown below:

Column 1, line 62 delete "approach provide" and replace with --approach provides--.Column 1, line 62 delete "approach provide" and replace with --approach provides--.

Column 3, line 3 delete "(bFGF;" and replace with --bFGF;--.

Column 3, line 42-43 delete "cerebral blood volume (CBF)," and replace with --cerebral blood flow (CBF),--.

Column 3, line 67 delete "certain regions if tissue" and replace with --certain regions of tissue--.

Column 4, line 30 delete "spin echo" and replace with --spin-echo--.

Column 6, line 41 delete "GLM algorithm." And replace with --GLM algorithms.--.

Column 7, line 49-50 delete "labeled a" and replace with --labeled a--.

Column 9, line 38 delete "(T2+ADC+DVI)" and replace --(T2+ADC+DWI)--.

Column 10, line 59 delete "were believed" and replace with --was believed--.

Column 11, line 54 delete "fast spin echo" and replace with --fast spin-echo--.

Column 12, line 26 delete "and B" and replace with --and ß--.

Column 12, line 28 delete "was change" and replace with --was changed--.

Signed and Sealed this

Fifteenth Day of August, 2006

JON W. DUDAS
*Director of the United States Patent and Trademark Office*